US006187976B1

United States Patent
Van Der Puy et al.

(10) Patent No.: US 6,187,976 B1
(45) Date of Patent: Feb. 13, 2001

(54) PROCESS FOR THE PREPARATION OF FLUORINE CONTAINING HYDROHALOCARBONS

(75) Inventors: Michael Van Der Puy, Erie County, NY (US); Richard Elmer Eibeck, Sedona, AZ (US); B. V. Bindu Madhavan, Erie County, NY (US); Hsueh Sung Tung, Erie County, NY (US); Lois Anne Short Ellis, Erie County, NY (US)

(73) Assignee: AlliedSignal Inc., Morristown, NJ (US)

( * ) Notice: Under 35 U.S.C. 154(b), the term of this patent shall be extended for 0 days.

This patent is subject to a terminal disclaimer.

(21) Appl. No.: 09/058,071

(22) Filed: Apr. 9, 1998

(51) Int. Cl.$^7$ .............................. C07C 19/08; C07C 17/08
(52) U.S. Cl. ........................... 570/176; 570/166; 570/168
(58) Field of Search ................................ 570/166, 169, 570/167, 168, 176, 178

(56) References Cited

U.S. PATENT DOCUMENTS

| | | | |
|---|---|---|---|
| 2,560,838 | 7/1951 | Arnold | 570/166 |
| 5,202,509 | 4/1993 | Laviron et al. | 570/167 |
| 5,347,059 | 9/1994 | Pennetreau et al. | 570/166 |
| 5,414,165 | * 5/1995 | Nappa et al. | 570/169 |
| 5,574,192 | 11/1996 | Van Der Puy et al. | 570/167 |
| 5,728,904 | 3/1998 | Van Der Puy et al. | 570/176 |
| 5,811,604 | 9/1998 | Benson et al. | 570/167 |
| 5,811,605 | * 9/1998 | Elsleich | 570/166 |

FOREIGN PATENT DOCUMENTS

| | | |
|---|---|---|
| 684687 | 4/1964 | (CA) . |
| 1418930 | 5/1961 | (DE) . |
| 522 639 A1 | 1/1993 | (FR) . |
| 1146463 | 3/1966 | (GB) . |

OTHER PUBLICATIONS

Journal Chemical Society, Asscher and Vofsi, Chlorine Activation by Redox–transfer. Part I. The Reaction Between Aliphatic Amines and Carbon Tetrachloride, 1961, pp. 2261–226.

Chemistry of Organic Fluorine Compounds, M. Hudlicky, Methods for Introducing Fluorine, p. 100.

Organic Chemistry, Fluorination of Organic Compounds with Anhydrous Hydrogen Fluoride I. The Preparation of Fluoroform and Certain Derivatives, W.B. Whalley, p. 3310.

Makromol. Chemistry, 185, 1583–1995 (1984), Telomerizationof Vinylidene Chloride I. Reaction With Carbon Tetrachloride by Redox Catalysis, M. Belbachir, B. Bouterin, Y. Pietrasanta and G. Rigal.

M.F. Shostakoviskii, N.A. Gershtein, and V.A. Neterman, Izv. Akad. Nauk SSSR, Otdel. Khim, Nauk, 378–381 (1956), vol. 21, No. 7, 1985 pp. 144–20 Reaction of Hydroxy–And Carbonyl Compounds with Sulfur Tetrafluoride.

Shanghai Institute of Organic Chemistry, Academia Sinica, Xuaxue Xuebao, vol. 38, No. 2, 4/80, pp. 175–184 Telomerizations of Vinylidene Fluoride with Perhaloalkanes and the Study of Their Products.

Plastics Manuf., vol. 114, 1991, 83236c $C_{3-5}$ Polyfluoroalkanes as Propellants and Blowing Agents, Sommerfeld, Claus Dieter DE 3,903,336.

Chemical Abstracts, vol. 114, 1991, 125031q Heat–transfer agents. FukoshimaMasato; Tateo (Asahi Glass Co., Ltd.), JP 02,272,086.

\* cited by examiner

Primary Examiner—Elli Peselev
(74) Attorney, Agent, or Firm—Colleen D. Szuch; Marie L. Collazo

(57) ABSTRACT

The invention relates to the preparation of 1-chloro-1,1,3,3-pentafluoropropane (HCFC-235fa), useful as an intermediate in the production of 1,1,1,3,3-pentafluoropropane (HFC-245fa). The invention further relates to a process for the preparation of HFC-245fa comprising reacting HCFC-235fa with hydrogen in the presence of a reduction catalyst wherein the said HCFC-235fa is prepared by reacting $CCl_3CHCCl_3$ with hydrogen fluoride in the presence of fluorination catalyst in either the liquid phase or the vapor phase.

23 Claims, No Drawings

PROCESS FOR THE PREPARATION OF FLUORINE CONTAINING HYDROHALOCARBONS

FIELD OF THE INVENTION

This invention is related to the preparation of fluorine containing hydrohalocarbons. Specifically, it relates to the manufacture of 1-chloro-1,1,3,3,3-pentafluoropropane (referred to in the art as HCFC-235fa) in the presence of a fluorination catalyst either in the liquid phase or vapor phase. HCFC-235fa is useful as an intermediate in the production of 1,1,1,3,3-pentafluoropropane (referred to in the art as HFC-245fa).

The invention also relates to a process for the preparation of 1,1,1,3,3-pentafluoropropane comprising the step of producing 1-chloro-1,1,3,3,3-pentafluoropropane by reaction of $CCl_3CH_2CCl_3$ with hydrogen fluoride in the presence of a fluorination catalyst either in the liquid phase or the vapor phase.

BACKGROUND OF INVENTION

Fluorine containing hydrohalocarbons are of current interest due to their potential to replace ozone depleting chlorofluorocarbons, which are used in a variety of applications including refrigerants, propellants, blowing agents, and solvents. Both HCFC-235fa and HFC-245fa are known to be useful as blowing agents. HFC-245fa has physical properties, including a boiling point of about 14° C., that makes it particularly attractive as a blowing agent, refrigerant or propellant. Its ability to function in a manner similar to CFC-11 ($CCl_3F$, b.p. 24° C.), a well known aerosol propellant at the time, was noted by Smith and Woolf in U.S. Pat. No. 2,942,036 (1960). European Patent Application EP 381 986 also states (using a generic formula) that $CF_3CH_2CF_2H$ may be used as a propellant or blowing agent. The use of HFC-245fa as a heat transfer agent is also mentioned in JP 02/272,086 (Chem. Abstr. 1991, 114, 125031q).

Previously, $CF_3CH_2CF_2Cl$ has been prepared by a liquid phase reaction of 1,1,1,3,3,3-hexachloropropane with HF in the presence of a catalyst, as disclosed in EP 0 522 639.

Commonly assigned U.S. Pat. No. 5,728,904 discloses the preparation $CF_3CH_2CF_2Cl$ by fluorination of $CCl_3CH_2CCl_3$ with HF in the presence of either $TiCl_4$ or $SnCl_4$ catalysts, followed by reduction to HFC-245fa.

The preparation of $CF_3CH_2CF_2Cl$ by the $BF_3$-catalyzed addition of HF to $CF_3CH=CFCl$ is also known (R. C. Arnold, U.S. Pat. No. 2,560,838; 1951). The source of $CF_3CH=CFCl$ was not disclosed.

HFC-245fa was first made by the reduction of $CF_3CCl_2CF_2Cl$ over a palladium catalyst (Smith and Woolf, U.S. Pat. No. 2,942,036, 1960). Materials exiting the reaction zone include $CF_3CH_2CHF_2$, $CF_3CH=CF_2$, $CF_3CCl=CF_2$, and unreacted starting material. The desired $CF_3CH_2CF_2H$ was formed in yields up to about 60%, but the source of the starting material was not disclosed.

Reduction of 1,1,1,3,3-pentafluoropropene was disclosed by Knunyants et al. (Chem. Abstr., 1961, 55, 349f). The yield of pentafluoropropane was 70%.

Burdon et al., J. Chem. Soc., C, 1969, 1739 disclose the formation of $CF_3CH_2CF_2H$, in low yield, during the elemental fluorination of tetrahydrofuran.

Commonly assigned U.S. Pat. No. 5,574,192 discloses the fluorination of $CCl_3CH_2CHCl_2$ with $HF/SbCl_5$ to produce HFC-245fa.

It is an object of this invention to provide a means of preparing 1-chloro-1,1,3,3,3 pentafluoropropane that is economical and amenable to large scale, using readily available raw materials.

It is a further object of this invention to provide a means of manufacturing 1,1,1,3,3-pentafluoropropane comprising reacting $CF_3CH_2CF_2Cl$ with hydrogen in the presence of a reduction catalyst wherein the said $CF_3CH_2CF_2Cl$ is prepared by reacting $CCl_3CH_2CCl_3$ with hydrogen fluoride in the presence of a fluorination catalyst in either the liquid phase or the vapor phase.

It is a further object of this invention to provide a means of manufacturing 1,1,1,3,3-pentafluoropropane comprising the following steps:

1) the formation of $CCl_3CH_2CCl_3$ by the reaction of $CCl_4$ with vinylidene chloride;
2) the conversion of $CCl_3CH_2CCl_3$ to $CF_3CH_2CF_2Cl$ by reaction with hydrogen fluoride (HF) in the presence of a fluorination catalyst either in the liquid phase or in the vapor phase; and
3) reduction of $CF_3CH_2CF_2Cl$ to $CF_3CH_2CF_2H$.

Each step is conducted under process conditions, i.e., temperature and pressure, sufficient to produce the desired product as discussed herein.

DETAILED DESCRIPTION

The telomerization of vinylidene chloride by reaction with $CCl_4$, is known in the art and has been studied in some detail. The telomerization reaction produces compounds of the formula $CCl_3(CH_2Cl)_nCl$, where n varies as needed for the products desired. The telomerization of vinylidene chloride can be initiated by several means, but initiation with metal salts, particularly of copper, has distinct advantages for the process of this invention. The copper salts are believed to initiate the reaction by first reacting with $CCl_4$, to produce a trichloromethyl radical which then combined with vinylidene chloride, initiating the telomerization (see for example, Assher and Vofsi, J. Chem. Soc., 1961, 2261 for a discussion of the mechanism). The copper salts also terminate the telomerization by chlorine atom transfer to the growing radical chain. Thus, the chain lengths are shortened considerably, compared to e.g., peroxide initiated telomerizations. For the reactions of interest here, telomers having 3 to 9 carbon atoms are obtained in excellent yield. Some control of the telomer distribution is feasible by controlling the reaction conditions, notably the ratio of $CCL_4$ to vinylidene chloride and the type of copper salt used (see for example Belbachir et al., Makromol. Chem. 1984, 185, 1583–1595). Thus, it is possible to obtain $CCl_3CH_2CCl_3$ with very little higher molecular weight telomers (see Example 1).

A variety of catalysts have been used in telomerization processes. To a large degree, many of these telomerization catalysts, including mixtures thereof, can be equivalent, and the choice of catalyst depends on cost, availability, and solubility in the reaction medium. For the telomerization reaction of this invention, it was discovered that salts of copper and iron are preferred. Overall, for the reaction of interest here, the more preferred catalysts are cuprous chloride, cupric chloride, or mixtures of the two or cuprous iodide. The amount of catalysts used in the telomerization reaction is at least about 0.1 mmol, and preferably, about 0.1 to about 50 mmol, per mole of saturated halogenated hydrocarbon (e.g., $CCl_4$ or $CCl_3CH_2CCl_3$) used. At very low concentrations, the reaction rate may be unacceptably slow, and very high catalyst concentrations may be wasteful due to the fact that the solubility limit may have been reached at even lower catalyst to $CCl_4$, ratios. Consequently, the more preferred amount of catalyst is about 1 to 20 mmol, per mole of saturated halogenated hydrocarbon.

It is also noted that a co-catalyst can be used in the telomerization process. Amines may be employed as co-catalysts, preferably in concentration of 1 to 10 moles per mole of metal catalyst (i.e. copper salt). Such amine co-catalysts include alkanol amines, alkyl amines and aromatic amines, for example ethanolamine, butyl amine, propyl amine, benzylamine, pyridine and the like.

The ratio of $CCl_4$ to vinylidene reactant will substantially alter the degree of polymerization, i.e. average value of n for compounds of the formula $CCl_3(CH_2Cl)_nCl$. Thus, for example, if the desired product has only one more —$CH_2CCl_2$— unit than the starting material, the ratio of $CCl_4$ (or $CCl_3CH_2CCl_3$) to vinylidene chloride should be relatively high (at least about 2, and preferably, about 2 to 5), so that higher molecular weight telomers are minimized. If the desired product has two or more —$CH_2CCl_2$— units than the starting material (e.g., $CCl_3(CH_2CCl_2)_2Cl$ from $CCl_4$), smaller ratios of $CCl_4$ to vinylidene chloride (about 0.3 to 1) should be used. The same rationale is used for a system employing vinylidene fluoride.

Useful temperatures for the telomerization reaction range from about 25° C. to about 225° C., preferably about 80° C. to about 170° C., so that, depending on reactant concentrations and catalyst activity, convenient reaction times will vary from a few hours to about one day. More preferred temperatures are in the about 125° C. to about 140° C. range.

Finally, a variety of solvents can be used. Any solvent which is inert to the reactants and the desired product can be used. Illustrative of such are acetonitrile, dimethylsulfoxide, dimethylformamide, tetrahydrofuran isopropanol, and tertiary butanol. We prefer acetonitrile due to its low cost, stability, easy recovery via distillation, and ability to dissolve sufficient amounts of inorganic catalyst salts. Primarily for the latter consideration, the amount of solvent is preferably from about one fourth to two thirds of the total volume, and more preferably one third to one half of the total volume. Otherwise, the amount of dissolved catalyst may be relatively low, or the output of product per run will be adversely affected due to a dilution effect.

In the second step, $CCl_3CH_2CCl_3$ is fluorinated to provide $CF_3CH_2CF_2Cl$. We have found that pentavalent antimony halides catalysts may be used to fluorinate $CCl_3CH_2CCl_3$ to provide $CF_3CH_2CF_2Cl$, but a critically narrow set of operating conditions, particularly with respect to temperature, mole ratio of HF to organic and catalyst concentration, must be employed to avoid over-fluorination. At high catalyst concentrations and/or high reaction temperatures the rate of the fluorination step is rapid, but selectivity declines to an unacceptable level. The higher the temperature, the more over-fluorinated product, $CF_3CH_2CF_3$ (referred to in the art as HFC-236fa), is produced.

Due to the temperature required, about 50° C. to about 100° C., preferably from about 60° C. to about 95° C., most preferably about 65° C. to about 90° C., the reactions are conducted under pressure. The pressure may be controlled by release of by-product HCl, during the reaction process in order to provide a margin of safety if needed depending on the limitations of the equipment being used. We have found it convenient to operate at pressures of about 50 to about 500 psig. The upper limit for pressure is generally a limitation of the available equipment. The reactor consisted of a stirred autoclave fitted with a packed column attached to a condenser maintained at about 0° C. to about −20° C. Excess pressure (HCl) is vented through a valve at the top of the condenser into a scrubber. At the end of the heating period, the product and remaining HF are vented through a valve on the autoclave head, which in turn is connected to an acid scrubber and cold traps to collect the product. Underfluorinated materials, such as $CF_2ClCH_2CF_2Cl$ may be recycled along with $CCl_3CH_2CCl_3$ in subsequent batch runs. The process may also be conducted in a continuous mode by removing a product stream at a rate equal to the rate at which the reactants are continuously fed into the reactor.

The mole ratio of HF to organic should be about 4/1 to about 20/1, preferably about 5/1 to about 9/1. Since over-fluorinated material, $CF_3CH_2CF_3$, is generally not desired, it is more advantageous to allow more under-fluorinated material (which can be recycled) in the crude product. Over-fluorinated product is kept low by smaller HF/organic ratios and lower reaction temperatures. In a batch mode, reaction time is also an important parameter to keep low over-fluorination. Under batch mode conditions, the reaction times range from about one to about 25 hours, preferably from about one to about ten hours, most preferably from about one to about five hours, and can be monitored by the rate of pressure (HCl) increase.

Pentavalent antimony halides are commercially available. Antimony pentachloride ($SbCl_5$) is most preferred because of its low cost and availability. Some catalyst deactivation is observed with $SbCl_5$, which is attributed generally to the formation of Sb (III) halides. Thus, chlorine is used as a co-feed in continuous liquid phase fluorination reactions to maintain the antimony in the +5 oxidation state. Pentavalent antimony mixed halides of the formula $SbCl_nF_{5-n}$, where n is 1 to 5 tend to be created in situ upon reaction with HF and are also preferred. The fluorination catalysts used in this invention preferably have a purity of at least about 97%. Although the amount of fluorination catalyst used may vary widely, we recommend using from about 5 to about 13 mol %, preferably about 6 to about 12 mol %, most preferably from about 7 to about 11 mol %, relative to $CCl_3CH_2CCl_3$.

The difficulty in conducting the fluorination of $CCl_3CH_2CCl_3$ so as to obtain chiefly $CF_3CH_2CF_2Cl$ can be appreciated by the fact that with HF alone (no fluorination catalyst) relatively low yields of the desired $CF_3CH_2CF_2Cl$ were obtained, the reaction affording primarily under-fluorinated products. With a liquid fluorination catalyst ($SbF_5$), a high yield of over-fluorinated product, $CF_3CH_2CF_3$, was obtained (see Examples 2 and 3).

For example, using $SbCl_5$ as the catalyst at a concentration of 1 mol % (relative to $CCl_3CH_2CCl_3$) and a reaction temperature of 100° C., the ratio of products was 43.3% $CF_3CH_2CF_2Cl$ and 54.5% $C_3H_2Cl_2F_4$ after 50 hours. By increasing the catalyst concentration to 5 mol %, a similar product distribution was achieved in 15 hours at the same temperature. By increasing the concentration of catalyst even further to 8.5 mol %, the product distribution was 51.4% $CF_3CH_2CF_2Cl$ and 44.1% $C_3H_2Cl_2F_4$ at a lower reaction temperature of 79° C. In each of the above cases, the amount of $CF_3CH_2CF_3$ was below 3%. However, further increasing the catalyst concentration to 16.7 mol % and lowering the temperature to 56° C. , did not prevent the formation of a substantial (8.5%) amount of the over-fluorinated product, $CF_3CH_2CF_3$. Thus, mole ratios (relative to organic) of about 13 to 18% resulted in unacceptable amounts of over-fluorinated product, while concentrations below about 5 mole % are less preferred due to reduced productivity. Good results were obtained at $SbCl_5$ concentrations of about 10 mole %.

Vapor phase fluorination reactions also may be used successfully. Reaction temperatures range from about 100° C. to about 400° C. , more preferably from about 250° C. to about 350° C. Suitable vapor phase catalysts principally include those based on chromium and aluminum salts and oxides (e.g. chrome oxide and aluminum fluoride) which may be modified with varying amounts of other transition metal salts and oxides such as those of manganese, nickel, cobalt, and iron. Thus, acceptable catalyst formulations may include, for example, mixtures of $Cr_2O_3/AlF_3/CoCl_2$, $Cr_2O_3/NiO/CoCl_2$, $Cr_2O_3/Al_2O_3$, $Cr_2O_3/AlF_3$, $Cr_2O_3/$carbon, $CoCl_2/Cr_2O_3/Al_2O_3$, $NiCl_2/Cr_2O_3/Al_2O_3$, $CoCl_2/AlF_3$ and $NiCl_2/AlF_3$. It is to be appreciated that the composition of the catalyst may change (e.g. undergo fluorination) during the initial fluorination process which will achieve a steady state composition after some time of operation. Such catalysts are conveniently handled in pelletized form (commonly ⅛" pellets). Chrome (III) oxide, supported or by itself, is the preferred catalyst.

The HF and hexachloropropane (HCC-230f) feeds are adjusted to the desired mole ratio, which preferably ranges from about 3:1 to about 100:1; more preferably from about 4:1 to about 50:1 and most preferably from about 5:1 to about 20:1.

Reaction pressure is not critical and can be superatmospheric, atmospheric or under vacuum. The vacuum pressure can be from about 5 torr to about 760 torr.

During the fluorination reaction, HCC-230f and HF are reacted in a vapor phase with the fluorination catalyst. The reactant vapor is allowed to contact the fluorination catalyst for from about 1 to about 120 seconds, preferably from about 1 to about 50 seconds, more preferably from about 1 to about 30 seconds. For purposes of this invention, "contact time" is the time required for the gaseous reactants to pass through the catalyst bed assuming that the catalyst bed is 100% void.

Before each use, the catalyst is preferably dried, pretreated and activated. It may also be advantageous to periodically regenerate the catalyst after prolonged use while in place in the reactor. Pre-treatment can be done by heating the catalyst to about 250 ° C. to about 430° C. in a stream of nitrogen or other inert gas. The catalyst may then be activated by treating it with a stream of HF diluted with a large excess of inert gas in order to obtain high catalyst activity. Regeneration of the catalyst may be accomplished by any means known in the art such as, for example, by passing air or air diluted with inert gas over the catalyst at temperatures of from about 100° C. to about 400° C., preferably from about 200° C. to about 375° C., for from about 8 hours to about 3 days, depending on the size of the reactor.

In the last step, $CF_3CH_2CF_2Cl$ is reduced to 1,1,1,3,3-pentafluoropropane. The reduction can be conveniently accomplished in a continuous flow system by passing vapors of $CF_3CH_2CF_2Cl$, along with hydrogen, over a reduction catalyst. Certain olefinic by-products of the fluorination step, e.g., $CF_3CH=CF_2$, also will be reduced to provide $CF_3CH_2CHF_2$.

Reduction catalysts include nickel, palladium, platinum and rhodium, which are usually supported on inert materials, such as carbon or alumina. These catalysts are available commercially and generally can be obtained having about 0.5 to about 20% by weight of the metal on the support material. More commonly, a loading of about 0.5 to about 5% weight percent is employed. Examples include 1% palladium on activated carbon granules and 0.5% platinum on ⅛" alumina pellets. The more preferred catalyst is palladium due to its lower cost compared to either platinum or rhodium.

While it is most convenient to operate to atmospheric pressure, this is not required. Both subatmospheric pressures or pressures up to about 100 atmospheres may be used, the latter especially in batch operations.

In the hydrogenation step it may be preferable to utilize a solvent, such as methanol, ethanol and acetic acid. A base may also be beneficial to neutralize the HCl produced. Any neutralizing agent can be used, e.g., sodium hydroxide, potassium hydroxide, sodium acetate and sodium carbonate.

Useful temperatures for vapor phase reductions range from about 100° C. to about 350° C., a more preferred range is from about 150° C. to about 250° C.

Based on reaction stoichiometry, the required ratio of hydrogen to organic is about 1 mole of hydrogen per mole of organic. From about 1 to about 50 times the stoichiometric ratio may be used. A ratio of about 2 to about 30 times the stoichiometric amounts can be used with satisfactory results.

The most desirable conditions for the reduction will vary and will depend, in part, on the activity of the catalyst (which depends on the type of metal used, its concentration on the support material, and the nature of the support material), and the contact or residence time in the reactor. Residence times may be adjusted by changing the reaction temperature, the catalyst volume, and the flow rates of hydrogen and/or organic material to be reduced. Useful contact times range from about 0.1 sec to about 2 minutes. In the present case, more preferred contact times range from about 10 to about 40 seconds at about 200° C. to about 225° C. and atmospheric pressure.

In the reduction of $CF_3CH_2CF_2Cl$ at atmospheric pressure and at temperatures of about 100° C. to about 325° C., both $CF_3CH_2CF_2H$ and $CF_3CH_2CF_2Cl$ are generally pre in the reactor effluent stream. The ratio of $CF_3CH_2CF_2H$ to $CF_3CH_2CF_2Cl$ increases with increasing reaction temperature. Continuous operation at high temperatures (>250° C.) is not very advantageous, due to potential gradual loss of the original catalyst activity. Consequently, the preferred method to achieve relatively high conversions of $CF_3CH_2CF_2Cl$ to $CF_3CH_2CF_2H$ is to increase the contact time, or equivalency, to recycle the product stream until the desired conversion is obtained. After separating the desired $CF_3CH_2CF_2H$ from $CF_3CH_2CF_2Cl$, the $CF_3CH_2CF_2Cl$ may be fed into the reactor again.

EXAMPLE 1

Preparation of $CCl_3CH_2CCl_3$

A Teflon-lined, magnetically stirred autoclave (575 mL capacity) was charged with 150 mL CC14, 150 mL $CH_3CN$, 0.51g CuCl and 0.51g $CuCl_2$ dihydrate. The autoclave was closed and evacuated briefly. Vinylidene chloride (57.7 g, 0.595 mol) was added via syringe and a rubber septum over a ball valve on the autoclave. The autoclave was then pressurized with nitrogen to 20 psig at room temperature. The mixture was heated over 1.75 h to 150° C. and maintained at 150° C. for 2 h. The stirrer speed was maintained at 350 rpm. After cooling the autoclave and contents to about 15° C., the contents were removed, diluted with 400 mL water, and the organic layer separated. The aqueous layer was extracted with 50 mL methylene chloride, and the combined organic layers washed with 100 mL brine. After drying ($Na_2SO_4$), the organic layer was concentrated by rotary evaporation to give 140.4 9 crude product. Distillation at 2.7 mm Hg gave 114.3 g $CCl_3CH_2CCl_3$, b.p. 63–65° C. (77% yield based on vinylidene chloride added). Its purity by GC analysis was 99.97%. 1H NMR ($CDCl_3$): singlet at 4.17 δ.

EXAMPLE 2

Fluorination of $CCl_3CH_2CCl_3$ with HF Alone

An autoclave was charged with 64 g (0.25 mole) $CCl_3CH_2CCl_3$ and 81 g (4.05 mole) HF and heated to 100° C. for 22 hours. The major volatile products, identified by GC-MS analysis, were $C_3H_2Cl_2F_4$, $C_3H_2Cl_3F_3$, and $C_3H_2Cl_4F_2$ isomers, along with some olefinic by-products. Note that no monochloro isomers were produced.

EXAMPLE 3

Fluorination of $CCl_3CH_2CCl_3$ with HF and $SbF_5$

A magnetically stirred autoclave fitted with a condenser maintained at –10° C. was charged with 7.6 g $SbF_5$ (0.035 mole) 64 g (0.255 mole) of $CCl_3CH_2CCl_3$, and 100 g (5.0 mole) of HF. The contents were then heated to 125 ° for 18 h. During the heating period, pressure in excess of 400 psig was periodically vented to an aqueous KOH scrubber which was attached to two cold traps maintained at –78° C. At the end of the heating period, the remainder of the contents were slowly vented. The cold traps contained 33.4 g of colorless liquid which consisted of 97.9% $CF_3CH_2CF_3$ and 0.5% $CF_3CH_2CF_2Cl$.

EXAMPLE 4

Liquid Phase Fluorination of $CCl_3CH_2CCl_3$

An autoclave was charged with 1 mole $CCl_3CH_2CCl_3$, 0.97 mol $SbCl_5$ and 7.55 mol HF, and heated for 1 hour at 52–72° C., 0.5 hour at 72–82° C. and finally 2 hours at 80–82° C. The operating pressure varied from 100 to 300 psig (periodic venting of HCl). The crude product consisted of 76.7% $CF_3CH_2CF_2Cl$, 4% $CF_3CH_2CF_3$ and 14.7% $C_3H_2Cl_2F_4$. The catalyst was then regenerated for the next batch by bubbling chlorine gas into the autoclave and stirring for 2 hours.

EXAMPLE 5

Continuous Liquid-phase Fluorination Process with HF/$SbCl_5$

In a typical liquid phase fluorination process, operating in a continuous mode, about 182 Kg of antimony pentachloride catalyst is charged to a 50 gal reactor. The reactor temperature is raised to 85° C. Reactants are then continuously fed into the reactor at the following rates: $CCl_3CH_2CCl_3$, 25.2 Kg/h; HF, 15 Kg/h; $Cl_2$, 0.68 Kg/h. The reactor pressure is maintained at about 150 psig by venting the product stream through a condenser, as was done in Example 3. The product stream consists of HCFC-235fa (1-chloro-1,1,3,3,3-pentafluoropropane), HFC-236fa (1,1,1,3,3,3-hexafluoropropane), 1,1,3,3,3-pentafluoropropene, HF, HCl and other minor amounts of organic by-products. The HCl, HF and residual chlorine are removed from the product stream by passing the effluent stream through a caustic scrubber. The acid-free product stream contains 60% HCFC-235fa, 10% HFC-236fa and 25% 1,1,3,3,3-pentafluoropropene.

EXAMPLE 6

Vapor Phase Fluorination of $CCl_3CH_2CCl_3$

In a typical run, a reactor of 1" diameter MONEL pipe is used. About 132 g (about 1.33 g/cc bulk density) chromium (III) oxide was charged to the reactor. The catalyst was dried and pretreated with HF before use. The reactor is preheated to the reaction temperature while anhydrous HF is fed into the reactor at atmospheric pressure. The organic feed ($CCl_3CH_2CCl_3$) was started when reactor reached 250° C. The HF and organic feeds were then adjusted to the desire rates. The HF/organic mole ratio is kept at about 7–8 to 1. The effluent product stream was analyzed by using an in-line GC. The product stream is fed to a caustic scrubber and the organic product mixture is collected. It contains about 50% HCFC-235fa, 20% HFC-236fa, 25% 1,1,3,3,3-pentafluoropropene and other minor amounts of organic by-products.

EXAMPLE 7

Reduction of $CF_3CH_2CF_2Cl$ at 200° C.

The reactor used in this Example consisted of an electrically heated glass column containing a catalyst bed comprised of a mixture of 10 cc 1% Pd on activated carbon (4–8 mesh) and 15 cc glass helices. Hydrogen was passed over the catalyst at 140 cc/min and $CF_3CH_2CF_2Cl$ was introduced at a rate of 2.25 g/h. The reaction temperature was 200° C. The material exiting the reactor was collected in a cold trap and consisted of approximately ⅓ $CF_3CH_2CF_2H$ and ⅔ unreacted $CF_3CH_2CF_2Cl$ by GC analysis. The single pass yield was about 33%.

EXAMPLE 8

Reduction of $CF_3CH_2CF_2Cl$ at 225° C.

Example 7 was repeated, except that the reaction temperature was increased to 225° C. The volatile material which collected in the cold trap consisted, by GC analysis, of 51% $CF_3CH_2CF_2H$. The remainder was primarily unreacted $CF_3CH_2CF_2Cl$. Distillation gave $CF_3CH_2CF_2H$, b.p. 14° C. The recovered $CF_3CH_2CF_2Cl$ was recycled to provide additional $CF_3CH_2CF_2H$.

EXAMPLE 9

Reduction of $CF_3CH_2CF_2Cl$ at Room Temperature

An autoclave was charged with a solution of 10 g KOH in 60 mL methanol, 0.5 g 1% Pd on carbon, and 25 g (0.15 mol) $CF_3CH_2CF_2Cl$. Stirring was begun and the autoclave pressurized to 250 psig with hydrogen. After 20 hours, the contents were cooled to 0° C. and excess hydrogen was bled off. The remaining volatile organic material was then transferred to a cold receiver under vacuum. Distillation of the crude material so obtained gave $CF_3CH_2CHF_2$. The yield was greater than 80%.

EXAMPLE 10

Reduction of the Product Stream from the Fluorination of $CCl_3CH_2CC_3$ with HF/$SbCl_5$ Operating in a Continuous Mode About 1 lb. of Pd/alumina catalyst is packed into a 2"×4' MONEL hydrogenation reactor. The acid-free product stream (about 100 lbs) obtained from Example 6 is fed to the hydrogenation reactor at a rate about 0.1 lb./hour along with a hydrogen feed of about 30 liters/hr. The temperature in the reactor, operated at 100 psi, is about 150° C. The exiting stream is passed through a caustic scrubber to remove HCl. Subsequently, the stream exiting the scrubber is fed into a 2" diameter distillation column. The distillation is conducted in a batch mode. HFC-245fa is isolated with >99% purity. The single pass yield is about 72% based on HCFC-235fa. Unreacted HCFC-235fa can be recycled to improve overall yield.

What is claimed is:

1. A process for the preparation of $CF_3CH_2CF_2Cl$ in the liquid phase comprising fluorinating $CCl_3CH_2CCl_3$ with hydrogen fluoride in a mole ratio of hydrogen fluoride to $CCl_3CH_2CCl_3$ of about 4/1 to about 20/1 in the presence of about 5 mol % to about 13 mol % of a pentavalent antimony halide fluorination catalyst of the formula $SbCl_nF_{5-n}$ where n is 1 to 5 wherein the fluorination reaction is conducted at a temperature of about 50° C. to about 100° C.

2. The process of claim 1 wherein the fluorination catalyst is $SbCl_5$.

3. The process of claim 1 wherein the fluorination catalyst is present in an amount of from about 7 mol % to about 11 mol % relative to $CCl_3CH_2CCl_3$.

4. The process of claim 1 wherein the reaction is conducted at about 75° C. to about 95° C.

5. The process of claim 1 wherein the reaction is conducted in a pressurized reactor at a pressure of about 50 to about 500 psig.

6. The process of claim 1 further comprising the step of recycling materials produced other than $CF_3CH_2CF_2Cl$.

7. The process of claim 1 or wherein the reaction is conducted in a continuous mode.

8. The process of claim 1 wherein the $CCl_3CH_2CCl_3$ is prepared by reacting $CCl_4$ with vinylidene chloride.

9. The process for the preparation of 1,1,1,3,3-pentafluoropropane comprising reacting $CF_3CH_2CF_2Cl$ with hydrogen in the presence of a reduction catalyst wherein the said $CF_3CH_2CF_2Cl$ is prepared by the process of claim 1.

10. A process for the preparation of 1,1,1,3,3-pentafluoropropane comprising reacting $CF_3CH_2CF_2Cl$ with hydrogen in the presence of a reduction catalyst wherein the said $CF_3CH_2CF_2Cl$ is prepared by a fluorination reaction comprising contacting $CCl_3CH_2CCl_3$ with hydrogen fluoride in the vapor phase in the presence of a fluorination catalyst.

11. The process of claim 10 wherein the fluorination reaction is conducted at about 100° C. to about 400° C.

12. The process of claim 10 wherein the molar ratio of hydrogen fluoride to $CCl_3CH_2CCl_3$ is about 3:1 to about 100:1.

13. The process of claim 10 wherein the molar ratio of hydrogen fluoride to $CCl_3CH_2CCl_3$ is about 5:1 to about 20:1.

14. The process of claim 10 wherein the $CCl_3CH_2CCl_3$ is contacted with hydrogen fluoride for about 1 to about 120 seconds.

15. The process of claim 10 wherein the $CCl_3CH_2CCl_3$ is contacted with hydrogen fluoride for about 1 to about 30 seconds.

16. The process of claim 10 wherein the fluorination catalyst is a transition metal salt, a transition metal oxide or a mixture thereof.

17. The process of claim 16 wherein the fluorination catalyst is a chromium oxide, an aluminum fluoride or a mixture thereof.

18. The process of claim 17 wherein the fluorination catalyst is modified with an oxide or a salt of a transition metal selected from the group of manganese, nickel, cobalt, iron and mixtures thereof.

19. The process of claim 18 wherein the fluorination catalyst is selected from the group consisting of $Cr_2O_3/AlF_3/CoCl_2$, $Cr_2O_3/NiO/CoCl_2$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$ and $NiCl_2/AlF_3$.

20. The process of claim 10 wherein the fluorination catalyst is chrome (III) oxide.

21. The process of claim 10 further comprising the step of recycling materials produced other than $CF_3CH_2CF_2Cl$.

22. The process of claim 10 wherein the fluorination reaction is conducted in a continuous mode.

23. The process of claim 10 wherein the $CCl_3CH_2CCl_3$ is prepared by reacting $CCl_4$ with vinylidene chloride.

* * * * *